United States Patent
Edwards

(10) Patent No.: US 8,430,643 B2
(45) Date of Patent: Apr. 30, 2013

(54) VOLUMETRIC FLUIDICS PUMP METHOD WITH TRANSLATING SHAFT

(75) Inventor: Craig Edwards, Mission Viejo, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 13/427,303

(22) Filed: Mar. 22, 2012

(65) Prior Publication Data

US 2012/0224979 A1  Sep. 6, 2012

Related U.S. Application Data

(62) Division of application No. 11/832,782, filed on Aug. 2, 2007, now Pat. No. 8,162,633.

(51) Int. Cl.
*F04B 43/12* (2006.01)
(52) U.S. Cl.
USPC .................. 417/53; 417/476; 417/477.7
(58) Field of Classification Search ............... 417/477.1, 417/477.3, 477.7, 477.8, 477.9, 477.11, 477.12, 417/53
See application file for complete search history.

(56) References Cited

U.S. PATENT DOCUMENTS

| | | | |
|---|---|---|---|
| 1,848,024 A * | 3/1932 | Owen | 417/477.8 |
| 2,123,781 A | 7/1938 | Huber | |
| 3,116,697 A | 1/1964 | Theodore | |
| 3,781,142 A | 12/1973 | Zweig | |
| 4,189,286 A | 2/1980 | Murry et al. | |
| 4,193,004 A | 3/1980 | Lobdell et al. | |
| 4,564,342 A | 1/1986 | Weber et al. | |
| 4,772,263 A | 9/1988 | Dorman et al. | |
| 4,773,897 A | 9/1988 | Scheller et al. | |
| 4,920,336 A | 4/1990 | Meijer | |
| 4,983,901 A | 1/1991 | Lehmer | |
| 5,006,110 A | 4/1991 | Garrison et al. | |
| 5,110,270 A | 5/1992 | Morrick | |

(Continued)

FOREIGN PATENT DOCUMENTS

| | | |
|---|---|---|
| EP | 56019 A1 | 7/1982 |
| EP | 1010437 A1 | 6/2000 |

(Continued)

OTHER PUBLICATIONS

English Abstract of JP57024482 from Feb. 9, 1982.*

(Continued)

*Primary Examiner* — Charles Freay
*Assistant Examiner* — Nathan Zollinger
(74) *Attorney, Agent, or Firm* — Abbott Medical Optics Inc.

(57) ABSTRACT

A pump for moving a fluid through a fluidics system includes a surface and channel disposed along at least a portion of the surface. The pump also includes a driving mechanism having a rotatable shaft and a plurality of haptics operably coupled to the shaft. A closed portion is formed in the channel as the channel is compressed between the surface and at least one of the haptics, the closed portion having a thickness between the surface and the haptic. The pump additionally has a circular path and a shaft path. The surface has a radius of curvature in the vicinity of the closed portion that is greater than the sum of a radius of the circular path and the thickness of the closed portion.

2 Claims, 3 Drawing Sheets

U.S. PATENT DOCUMENTS

| | | | |
|---|---|---|---|
| 5,125,891 A | 6/1992 | Hossain et al. |
| 5,195,960 A | 3/1993 | Hossain et al. |
| 5,195,961 A | 3/1993 | Takahashi et al. |
| 5,195,971 A | 3/1993 | Sirhan |
| 5,230,614 A | 7/1993 | Zanger et al. |
| 5,268,624 A | 12/1993 | Zanger |
| 5,282,787 A | 2/1994 | Wortrich |
| 5,342,293 A | 8/1994 | Zanger |
| 5,454,783 A | 10/1995 | Grieshaber et al. |
| 5,470,211 A | 11/1995 | Knott et al. |
| 5,520,652 A | 5/1996 | Peterson |
| 5,549,461 A | 8/1996 | Newland |
| 5,591,127 A | 1/1997 | Barwick, Jr. et al. |
| 5,657,000 A | 8/1997 | Ellingboe |
| 5,676,530 A | 10/1997 | Nazarifar |
| 5,676,650 A | 10/1997 | Grieshaber et al. |
| 5,693,020 A | 12/1997 | Rauh |
| 5,700,240 A | 12/1997 | Barwick, Jr. et al. |
| 5,733,256 A | 3/1998 | Costin |
| 5,747,824 A | 5/1998 | Jung et al. |
| 5,830,176 A | 11/1998 | Mackool |
| 5,899,674 A | 5/1999 | Jung et al. |
| 5,928,257 A | 7/1999 | Kablik et al. |
| 6,024,428 A | 2/2000 | Uchikata |
| 6,062,829 A | 5/2000 | Ognier |
| 6,086,598 A | 7/2000 | Appelbaum et al. |
| 6,117,126 A | 9/2000 | Appelbaum et al. |
| 6,150,623 A | 11/2000 | Chen |
| 6,179,829 B1 | 1/2001 | Bisch et al. |
| 6,260,434 B1 | 7/2001 | Holtorf |
| 6,360,630 B2 | 3/2002 | Holtorf |
| 6,436,072 B1 | 8/2002 | Kullas et al. |
| 6,452,120 B1 | 9/2002 | Chen |
| 6,452,123 B1 | 9/2002 | Chen |
| 6,491,661 B1 | 12/2002 | Boukhny et al. |
| 6,511,454 B1 | 1/2003 | Nakao et al. |
| 6,632,214 B2 | 10/2003 | Morgan et al. |
| 6,674,030 B2 | 1/2004 | Chen et al. |
| 6,962,488 B2 | 11/2005 | Davis et al. |
| 7,012,203 B2 | 3/2006 | Hanson et al. |
| 7,070,578 B2 | 7/2006 | Leukanech et al. |
| 7,169,123 B2 | 1/2007 | Kadziauskas et al. |
| 7,244,240 B2 | 7/2007 | Nazarifar et al. |
| 7,300,264 B2 | 11/2007 | Souza |
| 7,591,639 B2 * | 9/2009 | Kent ..................... 417/477.8 |
| 2001/0051788 A1 | 12/2001 | Paukovits et al. |
| 2002/0019607 A1 | 2/2002 | Bui |
| 2003/0073980 A1 | 4/2003 | Finlay et al. |
| 2003/0108429 A1 | 6/2003 | Angelini et al. |
| 2004/0037724 A1 | 2/2004 | Haser et al. |
| 2005/0054971 A1 | 3/2005 | Steen et al. |
| 2005/0069419 A1 | 3/2005 | Cull et al. |
| 2005/0070859 A1 | 3/2005 | Cull et al. |
| 2005/0118048 A1 | 6/2005 | Traxinger |
| 2005/0245888 A1 | 11/2005 | Cull |
| 2006/0145540 A1 | 7/2006 | Mezhinsky |
| 2006/0219049 A1 | 10/2006 | Horvath et al. |
| 2007/0016174 A1 | 1/2007 | Millman et al. |
| 2007/0049898 A1 | 3/2007 | Hopkins et al. |
| 2008/0033342 A1 | 2/2008 | Staggs |
| 2008/0066542 A1 | 3/2008 | Gao |
| 2008/0112828 A1 | 5/2008 | Muri et al. |
| 2008/0114289 A1 | 5/2008 | Muri et al. |
| 2008/0114290 A1 | 5/2008 | King et al. |
| 2008/0114291 A1 | 5/2008 | Muri et al. |
| 2008/0114300 A1 | 5/2008 | Muri et al. |
| 2008/0114311 A1 | 5/2008 | Muri et al. |
| 2008/0114312 A1 | 5/2008 | Muri et al. |
| 2008/0114372 A1 | 5/2008 | Edwards et al. |
| 2008/0114387 A1 | 5/2008 | Hertweck et al. |
| 2008/0125698 A1 | 5/2008 | Gerg et al. |

FOREIGN PATENT DOCUMENTS

| | | |
|---|---|---|
| EP | 1310267 A2 | 5/2003 |
| EP | 1704839 A1 | 9/2006 |
| EP | 1787606 A1 | 5/2007 |
| EP | 1867349 A1 | 12/2007 |
| EP | 1873501 A1 | 1/2008 |
| EP | 1900347 A1 | 3/2008 |
| GB | 2230301 A | 10/1990 |
| JP | 57024482 A * | 2/1982 |
| WO | WO9317729 A1 | 9/1993 |
| WO | WO9324082 A1 | 12/1993 |
| WO | WO9632144 A1 | 10/1996 |
| WO | WO9818507 A1 | 5/1998 |
| WO | WO9917818 A1 | 4/1999 |
| WO | WO0070225 A1 | 11/2000 |
| WO | WO0234314 A1 | 5/2002 |
| WO | WO2005084728 A2 | 9/2005 |
| WO | WO2005092023 A2 | 10/2005 |
| WO | WO2007143677 A2 | 12/2007 |
| WO | WO2008060859 A1 | 5/2008 |
| WO | WO2008060902 A1 | 5/2008 |

OTHER PUBLICATIONS

English Human Translation of JP57024482 from Feb. 9, 1982.*
"Phacoemulsification. Oct. 12, 2006. Wikipedia.com. Jun. 19, 2009 <http://en.wikipedia.org/wiki/Phacoemulsification>,".

* cited by examiner

VOLUMETRIC FLUIDICS PUMP METHOD WITH TRANSLATING SHAFT

This application is a divisional application and claims priority to U.S. application Ser. No. 11/832,782, entitled "Volumetric Fluids Pump with Translating Shaft Path", filed on Aug. 2, 2007, the entire contents of which are hereby incorporated by reference in their entirety for all purposes as if fully set forth herein.

BACKGROUND OF THE INVENTION

1. Field of the Invention

This invention relates generally to a volumetric fluidics pump, and more specifically to pump including a shaft or rotor that moves relative to a fluidic channel.

2. Description of the Related Art

Volumetric pumps may be advantageously utilized in a broad range of applications and offer various advantages such as precise control of a volumetric flow rate and preservation of a sterile environment. For example, in ocular surgical applications such as cataract surgery, peristaltic pumps are often used to maintain a critical balance between the flow of fluid into and out of the eye.

In a typical system, the peristaltic pump comprises a tube or channel that is continually closed between a ramp and one or more rollers disposed about a rotating pump head. As the pump head rotates, a first rollers engages the tube on an inlet side and draws fluid into a tube section that is subsequently sealed off by an adjacent, second roller. Once the tube section is sealed, the first roller opens the tube, thus allowing the second roller to push entrapped fluid out of the tubing section, while simultaneously drawing in new fluid. In order for the roller to close off the tubing, the mating ramp is arcuate in shape and generally has a radius of curvature that equals the sum of the radius of the circular roller path plus the thickness of the tube as it is squeezed between the ramp and one of the rollers.

One problem with such peristaltic pump designs is that in order to prepare the pump for operation, the ramp must be displaced from the pump head, the pump tubing arranged around the rollers, and the ramp moved back into place over tube. In addition, a relatively complex and expensive latching mechanism may be required to keep the tubing engaged between the rollers and ramp. Another potential problem is the time and difficulty involved in arranging the tubing around the rollers, which usually requires two hands.

In light of these problems, improved volumetric pumping devices and methods are needed that provide less expensive pumping components and simpler installation procedures.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE DRAWINGS

Embodiments of the present invention are directed to volumetric pump assemblies, procedures, and methods. Embodiments of the invention may be particularly suited for use in medical devices or surgical systems, for example, in ophthalmic surgical systems such as phacoemulsification systems used in preparing an eye for the implantation of an intraocular lens.

Volumetric pumps according to embodiments of the invention generally comprise a rotating pump head that includes a plurality of haptics, fingers, or rollers that contact a channel or tubing portion through which fluid is pumped. The pump may be configured to allow the haptics to move over or along a ramp surface that is flat or that has a radius of curvatures that is relatively large in comparison to the distance from the center of the pump head to a distal portion of the haptics used for transferring fluid through the pump. The ramp surface may be characterized by a single radius of curvature or may be a more complex shape, such as an aspheric shape and/or a shape characterized by two or more radii of curvature.

Figure 1:
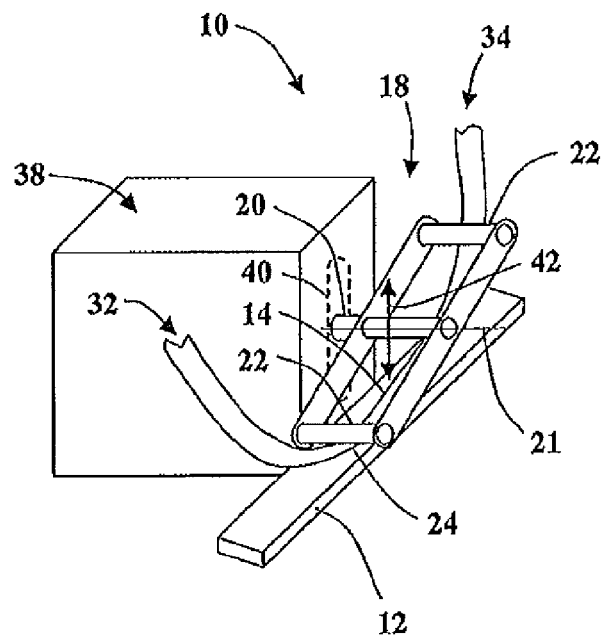
FIG. 1 is a perspective view of a pumping mechanism according to an embodiment of the present invention.
Figure 2:
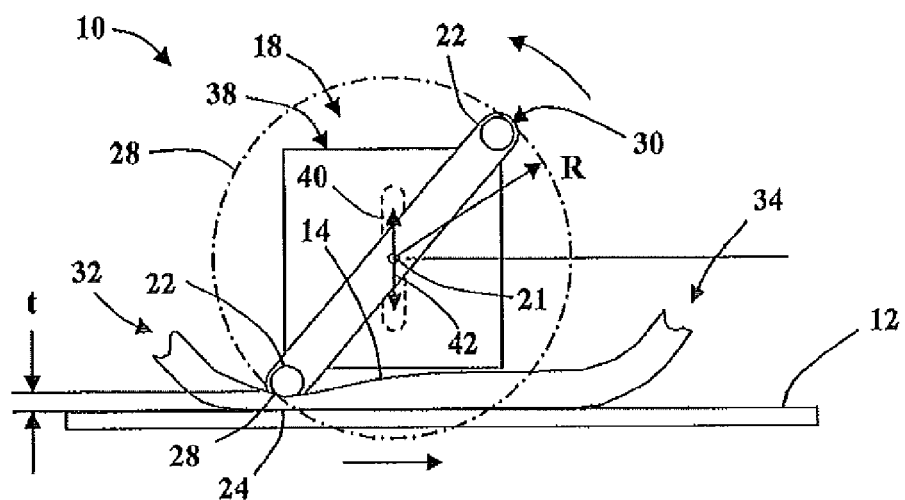
FIG. 2 is a front view of the pumping mechanism illustrated in FIG. 1

Referring to FIGS. 1 and 2, in certain embodiments of the present invention, a pumping system 10 comprises a surface 12, a channel 14 for transferring fluid, and a driving mechanism 18 that is configured transfer fluid through the channel 14 during operation of the pumping system 10. The driving mechanism 18 comprises a rotatable shaft 20 disposed about an axis 21 and a plurality of haptics 22 that are operably coupled to the shaft 20. The channel 14 comprises a closed portion 24 that is compressed between the surface 12 and at least one of the haptics 22, the closed portion 24 having a thickness t between the surface and an individual haptic 22. The haptics 22 are disposed inside a circular path 28 having a radius R, the distal portion of each haptic 22 traveling along the circular path 28 during operation of the pumping system 10. Conveniently, the circular path 28 may be defined as a locus of points about the axis 21 of the shaft 20 that arc traversed by a most distal point 30 of a haptic 22 as it revolves about the axis 21.

The driving mechanism 18 is generally configured to cause the haptics 22 to sequentially compress and close the channel 24, and to move along the surface 12 in a way that draws fluid in from an inlet side 32 and forces fluid out at an inlet side 34. The driving mechanism 18 may comprise a case or housing 38 that may include a driving motor, gear mechanism, linkage mechanism, and/or the like (not shown) that are configured to drive the shaft or rotor 20 and the haptics 22. The driving mechanism 18 may be configured so that the housing 38 moves with the shaft 20 during normal operation of the pumping system 10. Alternatively, as illustrated in FIGS. 1 and 2, the driving mechanism 18 may be configured so that the shaft moves relative to the housing 38 normal operation of the pumping system 10. In the later case, an aperture, slot, or opening 40 in the housing 38 may be provided to allow free movement of the shaft 20 relative to the housing 38.

The channel 14 may be made of a resiliently deformable and/or elastomeric tube or tubing portion through which fluid flows into and out of the pumping system 10. In certain embodiments, the channel 14 comprises a molded fluid channel, for example, like that disclosed in U.S. Pat. No. 6,962,488, which is herein incorporated by reference in its entirety. The channel 14 is generally part of a fluidic tubing system through which fluid flows. For example, the channel 14 may be part of a fluidics cassette that provides aspiration, irrigation, and other fluidic functions for an ocular surgical system, such as fluidics cassettes disclosed in co-pending U.S. patent application Ser. Nos. 11/530,306, 11/558,403, 11/558,434, 11/558,437, and 11/558,416, all of which are herein incorporated by reference in their entirety.

The haptics 22 may be in the form of rollers that engage and squeeze the channel 14 during operation of the driving mechanism 18. The rollers 22 are generally of made of a relatively hard and/or rigid material that deforms the relatively flexible channel 14. The rollers 22 may be rotatably mounted to a hub to reduce or eliminate rubbing between the rollers 22 and the exterior surface of the channel 14.

The surface 12 may be flat, as illustrated in FIGS. 1 and 2. Alternatively, the surface 12 may have a more complex profile along the direction of motion of the haptics 22. For example, the surface 12 may comprise an arcuate profile that is characterized by one or more radii of curvature and/or defined by a polynomial, trigonometric, or some other function. In any event, surface 12 is generally relatively flat compared to a conventional peristaltic pumping system. The relatively flat profile of the surface 12 allows the channel 14 to be easily arranged within the pumping system 10 during preparation and use. In some embodiments, the radius of curvature of the surface 12 in the vicinity of the closed potion 24 is greater than the sum of the radius R of the circular path 28 plus the thickness t of the closed portion 24. Because of this geometric relationship, the shaft 20 may be moved during operation in a direction that is generally normal to the surface 12, thus maintaining the closed portion 24 as the haptics rotate about the shaft 20.

In this regard, the pumping system 10 further comprises a shaft path 42 that is traversed by shaft 20 during operation of the pumping system 10 or driving mechanism 18. The resulting motion of each haptics 22, relative to a fixed reference (e.g., relative to the surface 12), is a combination of motion of each haptic 22 about the shaft 20 (e.g., along the circular path 28) and the motion of the shaft 20 along the shaft path 42. The motion of each haptic 22 results in a haptic path portion that is along at least a portion of the surface 12 and allows each haptic 22 to keep the channel 14 closed until the succeeding haptic 22 also closes the channel 14.

Figures 3A, 3B, 3C:
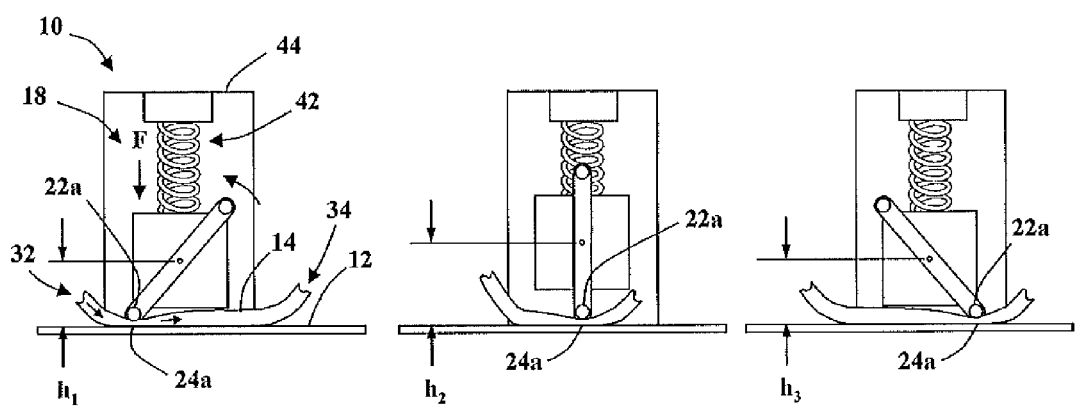
FIGS. 3A-3E are front views of the pumping mechanism illustrated in FIG. 1 and show operation of pump as it draws fluid therethrough.

The operation of the pumping system 10 and path of the haptics 22 along the surface 12 may be illustrated with reference to FIGS. 3A-3E. In FIG. 3A, a first haptic 22a comes into contact with the channel 14 and forms a first closed portion 24a. When the first closed portion 24a is initially formed, the axis 21 of the rotatable shaft 20 is at a height $h_1$ above the surface 12. As the driving mechanism 18 rotates about the axis 21 (counter clockwise in FIGS. 3A-3E), fluid is drawn into the pumping system 10 from the inlet side 32 and is pushed out of the outlet side 34. In order to maintain the first closed portion 24a during rotation of the shaft 20, a bias force F may be provided to overcome the resiliency of the channel 14. In the illustrated embodiment shown in FIGS. 3A-3E, the bias force is provided by a spring 42 that is coupled on one end to the housing 38 and on the other end to a base 44 that is generally fixed relative to the surface 12. Alternatively or additionally, the bias force may be produced by the mere weight of the driving mechanism 18, by a cam, and/or some other biasing device or mechanism is used to provide a predetermined biasing force F that is suitable for closing off the channel 14 between the surface 12 and the first haptic 22a.

Figures 3D, 3E:
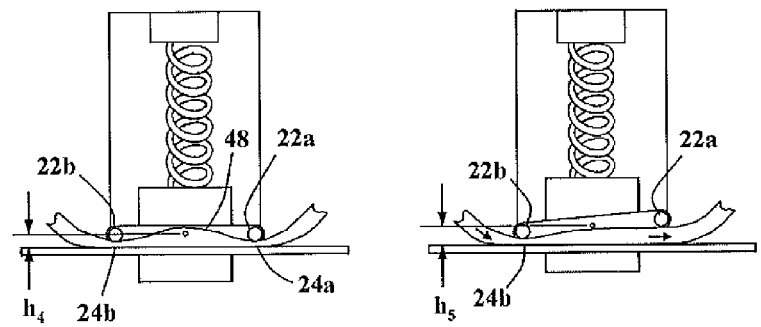

As the driving mechanism 18 continues to rotate, the height of the axis 21 above the surface 12 increases to a maximum height $h_2$. As illustrate in FIG. 3C, further rotation of mechanism 18 results in a decrease in height (e.g., height $h_3$) as the bias force F pushes the axis 21 toward the surface 12 to maintain the first closed portion 24a of the channel 14. As illustrated in FIG. 3D, the mechanism 18 continues to rotate until a second haptic 22b contacts the channel 14 and forms a second closed portion 24b that defines a closed volume 48 of fluid. At this point, the height of the axis 21 above the surface 12 reaches a minimum height $h_4$. Referring to FIG. 3E, further rotation results in a new cycle in which fluid from the closed volume 48 flows past the haptic 22a as the channel 14 opens between the surface 12 and the haptic 22a.

Figure 4A:
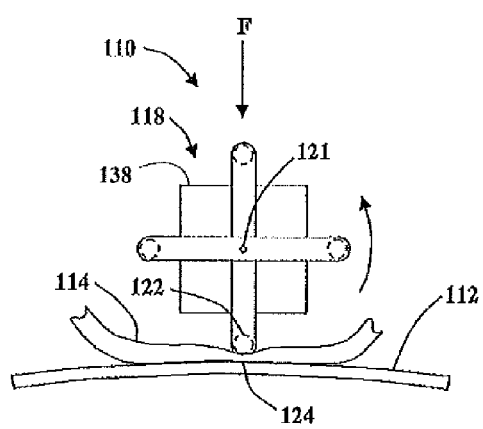
FIG. 4 is a front view of a pumping mechanism according to another embodiment of the present invention.
Figure 4B:
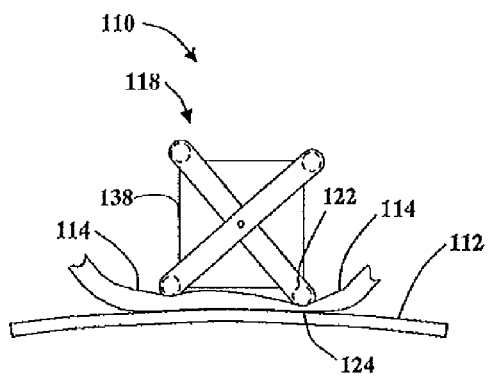

Pumping systems according to embodiments of the invention may include features other than those illustrated for the pumping system 10. Referring to FIGS. 4a and 4b, another embodiment of the invention comprises a pumping system 110 includes a driving mechanism 118 that comprises a housing 138 and four haptics 122 disposed about an axis 121. The pumping system 110 also includes a channel 114 disposed between the haptics 122 and a surface 112 that has a convex shape. As illustrated by comparing FIG. 4A with FIG. 4B, the entire driving mechanism 118 moves in a direction that is substantially perpendicular to the surface 112 as the driving mechanism rotates about the axis 121. Similar to the pumping mechanism 10, the pumping mechanism 110 provides a closed portion 124 of the channel 114 that is configured to draw fluid through the pumping mechanism 110 as the driving mechanism 118 moves succeeding haptics along the surface 112.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A method of pumping a fluid, comprising:
   providing a surface, a shaft, a shaft path, and a plurality of haptics operably coupled to the shaft;
   disposing a channel between the surface and the haptics, wherein the channel is configured to have a closed portion when compressed between the surface and one of the haptics, the closed portion having a thickness defined by a distance between the surface and the haptic that closes the channel;
   moving the haptics along a circular path about the shaft;
   moving the shaft relative to the surface and the shaft path, wherein the surface has a radius of curvature in the vicinity of the channel that is greater than the sum of a radius of the circular path and the thickness of the closed portion;
   while moving the haptics and the shaft, traversing at least one of the haptics along the surface so that the at least one haptic maintains the channel in a closed condition,
   wherein a length from a center of the shaft to a distal end of one of the haptics is greater than the distance between the surface and the center of the shaft when the channel is in its least compressed state during rotation of the shaft;
   moving the shaft along the shaft path radially away from the surface when at least one of the haptics traverses along a portion of the surface.

2. The method of claim 1, further comprising, traversing a first haptic of the plurality and a second haptic of the plurality along the surface so as to produce a closed fluid volume within the channel, the closed fluid volume being disposed between the first haptic and the second haptic.

\* \* \* \* \*